US008399625B1

(12) United States Patent
Escher

(10) Patent No.: US 8,399,625 B1
(45) Date of Patent: Mar. 19, 2013

(54) ACCEPTOR FRAMEWORK FOR CDR GRAFTING

(75) Inventor: Dominik Escher, Zug (CH)

(73) Assignee: ESBATech, an Alcon Biomedical Research Unit, LLC, Schlieren (CH)

( * ) Notice: Subject to any disclaimer, the term of this patent is extended or adjusted under 35 U.S.C. 154(b) by 26 days.

(21) Appl. No.: 12/823,551

(22) Filed: Jun. 25, 2010

Related U.S. Application Data

(60) Provisional application No. 61/220,508, filed on Jun. 25, 2009.

(51) Int. Cl.
*C12P 21/08* (2006.01)
(52) U.S. Cl. .................................................. 530/387.3
(58) Field of Classification Search .................. None
See application file for complete search history.

(56) References Cited

U.S. PATENT DOCUMENTS

| 4,704,362 | A | 11/1987 | Itakura et al. |
| 5,225,539 | A | 7/1993 | Winter |
| 5,304,489 | A | 4/1994 | Rosen |
| 5,741,957 | A | 4/1998 | Deboer et al. |
| 5,837,821 | A | 11/1998 | Wu |
| 5,849,992 | A | 12/1998 | Meade et al. |
| 7,429,487 | B2 | 9/2008 | Pytela et al. |

FOREIGN PATENT DOCUMENTS

| WO | 8601533 | | 3/1986 |
| WO | 9409817 | | 5/1994 |
| WO | 0148017 | A1 | 7/2001 |
| WO | 0202781 | A1 | 1/2002 |
| WO | 03097697 | A2 | 11/2003 |
| WO | 2004016740 | A2 | 2/2004 |
| WO | 2005016950 | A1 | 2/2005 |
| WO | 2008110348 | A1 | 9/2008 |
| WO | 2008144757 | A1 | 11/2008 |
| WO | 2009000098 | A2 | 12/2008 |
| WO | 2009000099 | A2 | 12/2008 |
| WO | 2009007861 | A1 | 1/2009 |
| WO | 2009155725 | A1 | 12/2009 |

OTHER PUBLICATIONS

Mariuzza et al. (Annu. Rev. Biophys. Biophys. Chem. 1987; 16: 139-159).*
Gussow et al. (Methods in Enzymology. 1991; 203: 99-121).*
Rudikoff et al (Proc. Natl. Acad. Sci. USA 1982 vol. 79: p. 1979-1983).*
MacCallum et al. (J. Mol. Biol. Oct. 11, 1996; 262 (5): 732-745).*
Holm et al. (Mol. Immunol. Feb. 2007; 44 (6): 1075-1084).*
Alfthan et al.; "Properties of a single-chain antibody containing different linker peptides"; Protein Engineering; vol. 8; No. 7; pp. 725-731 (1995).
Auf Der Maur et al; "Antigen independent selection of stable intracellular single-chain antibodies"; FEBS Letters: vol. 508; pp. 407-412 (2001).
Bird et al; "Single-chain antigen-binding proteins"; Science; vol. 242; pp. 423-426; (Oct. 21, 1988).
Boulianne et al.; "production of functional chimaeric mouse/human antibody"; Letters to nature; Nature; vol. 312; pp. 643-646 (Dec. 13, 1984).
Carter et al; "Improved oligonucleotide site-directed mutagenesis using M13 vectors"; Nucleic Acids Research; vol. 13; No. 12; pp. 4431-4443; (1985).
Choi et al; "Recombinant chimeric OKT3 scFv IgM antibodies mediate immune suppression while reducing T cell activation in vitro"; Eur. J. immunol.; vol. 31; pp. 94-106 (2001).
Clark; Antibody humanization: a case of the 'Emperor's new clothes'?; review; Immunology today; vol. 21; No. 8; pp. 397-402.
Co et al; "Chimeric and humanized antibodies with specificity for the CD33 antigen"; The Journal of Immunology; vol. 148; pp. 1149-1154 (Feb. 15, 1992).
Dillman et al.; "Human anti-mouse antibody response in cancer patients following single low-dose injections of radiolabeled murine monoclonal antibodies"; vol. 9; No. 1; pp. 17-29 (1994).
Dumoulin et al; "Single-domain antibody fragments with high conformational stability"; Protein Science; vol. 11; pp. 500-515 (2002).
Hamera-Casterman et al; "Naturally occurring antibodies devoid of light chains"; Letters to Nature; vol. 363; pp. 446-448 (Jun. 3, 1993).
Ho et al; "Site-directed mutagenesis by overlap extension using the polymerase chain reaction"; Gene; vol. 77; pp: 51-59 (1989).
Holliger et al; "Diabodies: small bivalent and bispecific antibody fragments"; Proc. Natl. Acad. Sci.; vol. 90; pp. 6444-6448 (Jul. 1993).
Honegger and Pluckthun; "Yet another numbering scheme for immunoglobulin variable domains: an automatic modeling and analysis tool"; J. Mol. Biol.; vol. 309; pp. 657-670 (2001).
Hu et al; "Minibody: a novel engineered anti-carcinoembryonic antigen antibody fragment (single-chain Fv-CH3) which exhibits reapid, high-level targeting of xenografts"; Cancer Research; vol. 56; pp. 3055-3061 (Jul. 1, 1996).
Houston et al; "Protein engineering of antibody binding sites: recovery of specific activity in an anti-digoxin single-chain Fv analogue produced in *Escherichia coli*"; Proc. natl. Acad. Sci.; vol. 85; pp. 5879-5883 (Aug. 1988).
Kipriyanov et al; "Bispecific tandem diabody for tumor therapy with improved antigen binding and pharmacokinetics"; J. Mol. Biol.; vol. 293; pp. 41-56 (1999).
Knappik et al; "Fully synthetic human combinatorial antibody libraries (HuCAL) based on modular consensus frameworks and CDRs randomized with trinucleotides"; J. Mol. Biol.; vol. 296; pp. 57-86 (2000).
Kunkel; Rapid and efficient site-specfiic mutagenesis without phenotypic selection; Proc. Natl. Acad. Sci.; vol. 82; pp. 488-492 (Jan. 1985).
Lobuglio et al; "Mouse/human chimeric monoclonal antibody in man: Kinetics and immune response"; Proc. Natl.; Acad. Sci.; vol. 86; pp. 4220-4224 (Jun. 1989).
Milenic et al; "Construction, binding properties, metabolism, and tumor targeting of a single-chain Fv derived form the pancarcinoma monoclonal antibody CC49"; Cancer Research; vol. 51; pp. 6363-6371 (Dec. 1, 1991).

(Continued)

*Primary Examiner* — Brad Duffy
(74) *Attorney, Agent, or Firm* — Jason J. Derry

(57) ABSTRACT

The present invention relates to an antibody acceptor framework and to methods for grafting non-human antibodies, e.g., rabbit antibodies, using a particularly well suited antibody acceptor framework. Antibodies generated by the methods of the invention are useful in a variety of diagnostic and therapeutic applications.

6 Claims, 2 Drawing Sheets

OTHER PUBLICATIONS

Needleman and Wunsch; "A general method applicable to the search for similarities in the amino acid sequence of two proteins"; J. Mol. Biol.; vol. 48; pp. 443-453 (1970).

Pantolano et al; "Conformational stability, folding, and ligand-binding affinity of single-chain Fv immunoglobulin fragments expressed in *Eschericha coli*"; Biochemistry; vol. 30; pp. 10117-10125 (1991).

Queen et al; "Cell-type specific regulation of a k immunoglobulin gene by promoter and enhancer elements"; Immunological Reviews; pp. 49-68 (1986).

Riechmann et al; "Reshaping human antibodies for therapy"; Nature; vol. 332; pp. 323-327 (Mar. 24, 1988).

Schroff et al; "Human anti-murine immunoglobulin responses in patients receiving monoclonal antibody therapy"; Cancer Research; vol. 45; pp. 879-885 (Feb. 1985).

Shawler et al; "Human immune response to multiple injections of murine monoclonal IgG1"; The Journal of Immunology; vol. 135; No. 2; pp. 1530-1535 (Aug. 1985).

Spieker-Polet et al; "Rabbit monoclonal antibodies: generating a fusion partner to produce rabbit-rabbit hybidomas"; Proc. Natl. Acad. Sci.; vol. 92; pp. 9348-9352 (Sep. 1995).

Takkinen et al; "An active single-chain antibody containing a cellulase linker domain is secreted by *Escherichia coli*"; Protein Engineering; vol. 4; No. 7; pp. 837-841 (1991).

Vallette et al; "Construction of; mutant and chimeric genes using the polymerase chain reaction"; Nucleic Acids Research; vol. 17; No. 2; pp. 723-733 (1989).

Ward et al; "Binding activities of a repertoire of single immunoglobulin variable domains secreted form *Escherichia coli*"; Letters to Nature; vol. 341; pp. 544-546 (Oct. 12, 1989).

Wells et al; "Cassette mutagenesis: an efficient method for generation of multiple mutations at defined sites"; Gene; vol. 34; pp. 315-323 (1985).

* cited by examiner

ACCEPTOR FRAMEWORK FOR CDR GRAFTING

The present application claims the benefit of U.S. Provisional Patent Application Ser. No. 61/220,503, filed on Jun. 25, 2009, the disclosure of which is specifically incorporated by reference herein.

BACKGROUND OF THE INVENTION

Monoclonal antibodies, their conjugates and derivatives are hugely commercially important as therapeutic and diagnostic agents. Non-human antibodies elicit a strong immune response in patients, usually following a single low dose injection (Schroff, 1985 Cancer Res 45:879-85, Shawler. J Immunol 1985 135:1530-5; Dillman, Cancer Biother 1994 9:17-28). Accordingly, several methods for reducing the immunogenicity of murine and other rodent antibodies as well as technologies to make fully human antibodies using e.g. transgenic mice or phage display were developed. Chimeric antibodies were engineered, which combine rodent variable regions with human constant regions (e.g., Boulianne Nature 1984 312:643-6) reduced immunogenicity problems considerably (e.g., LoBuglio, Proc Natl Acad Sci 1989 86:4220-4; Clark, Immunol Today 2000 21:397-402). Humanized antibodies were also engineered, in which the rodent sequence of the variable region itself is engineered to be as close to a human sequence as possible while preserving at least the original CDRs, or where the CDRs from the rodent antibody were grafted into framework of a human antibody (e.g., Riechmann, Nature 1988 332:323-7; U.S. Pat. No. 5,693,761). Rabbit polyclonal antibodies are widely used for biological assays such as ELISAs or Western blots. Polyclonal rabbit antibodies are oftentimes favored over polyclonal rodent antibodies because of their usually much higher affinity. Furthermore, rabbit oftentimes are able to elicit good antibody responses to antigens that are poorly immunogenic in mice and/or which give not rise to good binders when used in phage display. Due to these well-known advantages of rabbit antibodies, they would be ideal to be used in the discovery and development of therapeutic antibodies. The reason that this is not commonly done is mainly due to technical challenges in the generation of monoclonal rabbit antibodies. Since myeloma-like tumors are unknown in rabbits, the conventional hybridoma technology to generate monoclonal antibodies is not applicable to rabbit antibodies. Pioneering work in providing fusion cell line partners for rabbit antibody-expressing cells has been done by Knight and colleagues (Spieker-Polet et al., PNAS 1995, 92:9348-52) and an improved fusion partner cell line has been described by Pytela et al. in 2005 (see e.g. U.S. Pat. No. 7,429,487). This technology, however, is not widely spread since the corresponding know-how is basically controlled by a single research group. Alternative methods for the generation of monoclonal antibodies that involve the cloning of antibodies from selected antibody-expressing cells via RT-PCR are described in the literature, but have never been successfully reported for rabbit antibodies.

Rabbit antibodies, like mouse antibodies are expected to elicit strong immune responses if used for human therapy, thus, rabbit antibodies need to be humanized before they can be used clinically. However, the methods that are used to make humanized rodent antibodies cannot easily be extrapolated for rabbit antibodies due to structural differences between rabbit and mouse and, respectively, between rabbit and human antibodies. For example, the light chain CDR3 (CDRL3) is often much longer than previously known CDRL3s from human or mouse antibodies.

There are few rabbit antibody humanization approaches described in the prior art, which are, however, no classical grafting approach in which the CDRs of a non-human donor are transplanted on a human acceptor antibody. WO 04/016740 describes a so-called "resurfacing" strategy. The goal of a "resurfacing" strategy is to remodel the solvent-accessible residues of the non-human framework such that they become more human-like. Similar humanization techniques for rabbit antibodies as described in WO 04/016740 are known in the art. Both WO08/144,757 and WO05/016950 disclose methods for humanizing a rabbit monoclonal antibody which involve the comparison of amino acid sequences of a parent rabbit antibody to the amino acid sequences of a similar human antibody. Subsequently, the amino acid sequence of the parent rabbit antibody is altered such that its framework regions are more similar in sequence to the equivalent framework regions of the similar human antibody. In order to gain good binding capacities, laborious development efforts need to be made for each immunobinder individually.

A potential problem of the above-described approaches is that not a human framework is used, but the rabbit framework is engineered such that it looks more human-like. Such approach carries the risk that amino acid stretches that are buried in the core of the protein still might comprise immunogenic T cell epitopes.

To date, the applicants have not identified a rabbit antibody, which was humanized by applying state-of-the-art grafting approaches. This might be explained by fact that rabbit CDRs may be quite different from human or rodent CDRs. As known in the art, many rabbit VH chains have extra paired cysteines relative to the murine and human counterparts. In addition to the conserved disulfide bridge formed between cys22 and cys92, there is also a cys21-cys79 bridge as well as an interCDR S-S bridge formed between the last residue of CDRH1 and the first residue of CDR H2 in some rabbit chains. Besides, pairs of cysteine residues are often found in the CDR-L3. Moreover, many rabbit antibody CDRs do not belong to any previously known canonical structure. In particular the CDR-L3 is often much longer than the CDR-L3 of a human or murine counterpart.

Hence, the grafting of non-human CDRs antibodies into a human framework is a major protein engineering task. The transfer of antigen binding loops from a naturally evolved framework to a different artificially selected human framework must be performed so that native loop conformations are retained for antigen binding. Often antigen binding affinity is greatly reduced or abolished after loop grafting. The use of carefully selected human frameworks in grafting the antigen binding loops maximizes the probability of retaining binding affinity in the humanized molecule (Roguzka et al 1996). Although the many grafting experiments available in the literature provide a rough guide for CDR grafting, it is not possible to generalize a pattern. Typical problems consist in loosing the specificity, stability or producibility after grafting the CDR loops.

Accordingly, there is an urgent need for improved methods for reliably and rapidly humanizing rabbit antibodies for use as therapeutic and diagnostic agents. Furthermore, there is a need for human acceptor frameworks for reliably humanizing rabbit antibodies, providing functional antibodies and/or antibody fragments with drug-like biophysical properties.

SUMMARY OF THE INVENTION

It has surprisingly been found that a highly soluble and stable human antibody framework identified by a Quality Control (QC) assay (as disclosed in WO 0148017 and in Auf der Maur et al (2001), FEBS Lett 508, p. 407-412) is particularly suitable for accommodating CDRs from other non-human animal species, for example, rabbit CDRs. Accordingly, in a first aspect, the invention provides the heavy chain variable regions of a particular human antibody (the so called, "a58" VH framework sequence) which is especially suitable as acceptor for CDRs from a variety of antibodies, in particular from rabbit antibodies, of different binding specificities, independent of whether a disulfide bridge is present in a CDR or not.

Humanized immunobinders generated by the grafting of rabbit CDRs into this highly compatible variable chain framework consistently and reliably retain the spatial orientation of the rabbit antibodies from which the donor CDRs are derived. Therefore, no structurally relevant positions of the donor immunobinder need to be introduced into the acceptor framework. Due to these advantages, high-throughput humanization of rabbit antibodies with no or little optimization of the binding capacities can be achieved.

Accordingly, in another aspect, the invention provides methods for grafting rabbit and other non-human CDRs, into the soluble and stable light chain and/or heavy chain human antibody framework sequences disclosed herein, thereby generating humanized antibodies with superior biophysical properties. In particular, immunobinders generated by the methods of the invention exhibit superior functional properties such as solubility and stability.

DETAILED DESCRIPTION OF THE INVENTION

Definitions

Figure 1:
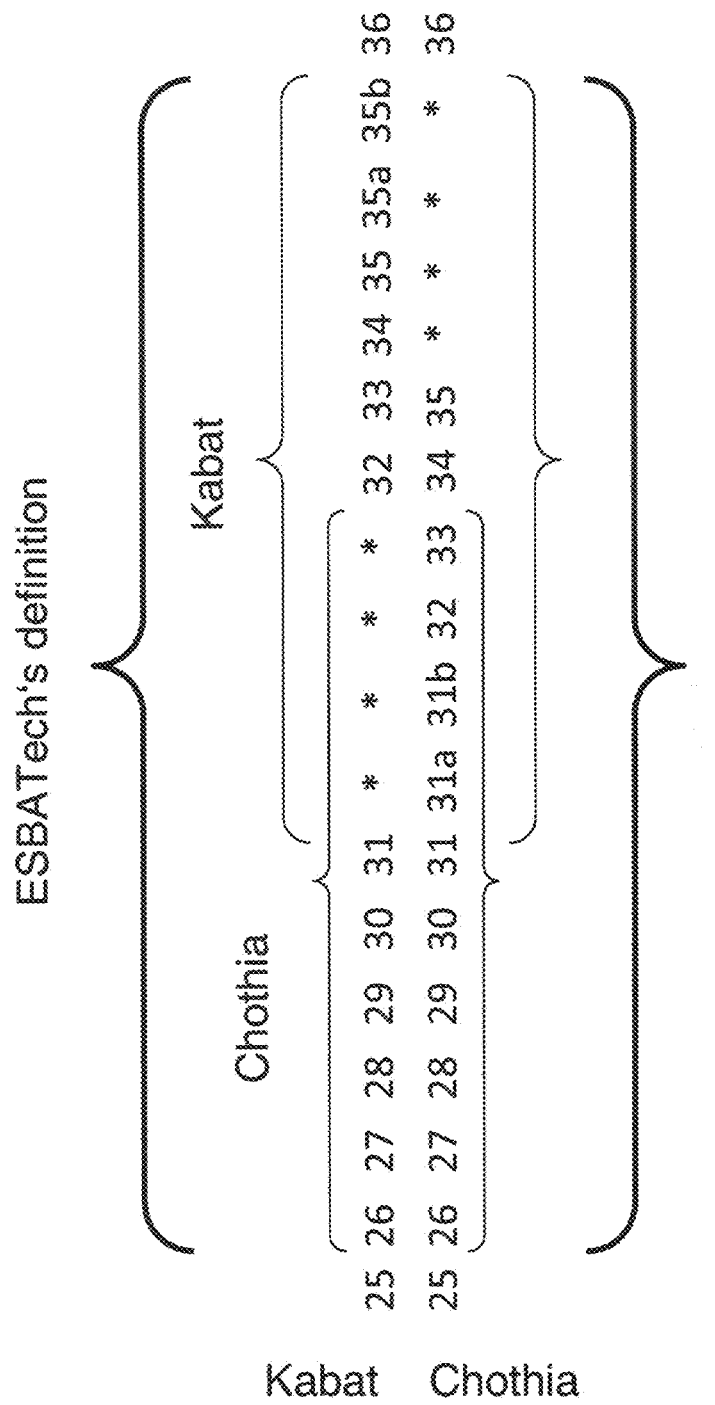
FIG. 1 depicts the CDR H1 definition used herein for grafting antigen binding sites from rabbit monoclonal antibodies into the highly soluble and stable human antibody frameworks.
Figure 2:
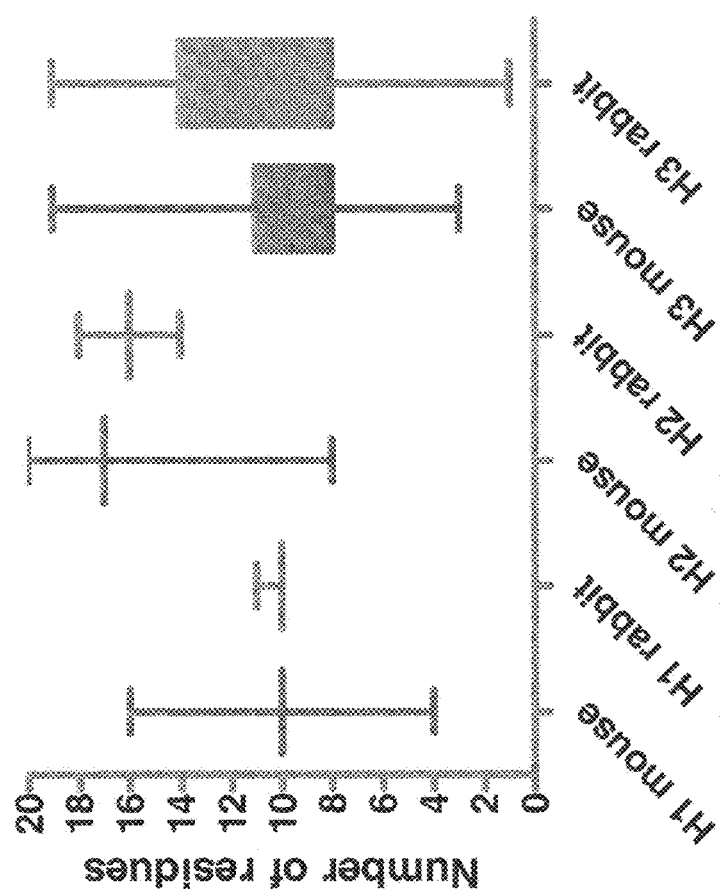
FIG. 2: An analysis of rabbit antibody sequences extracted from the Kabat database confirms that CDR3 of the variable heavy chain is typically by three amino acids longer than its murine counterpart.

In order that the present invention may be more readily understood, certain terms will be defined as follows. Additional definitions are set forth throughout the detailed description.

The term "antibody" refers to whole antibodies and any antigen binding fragment. The term "antigen binding polypeptide" and "immunobinder" are used simultaneously herein. An "antibody" refers to a protein, optionally glycosylated, comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antibody portion") refers to one or more fragments of an antibody that retain the ability to specifically bind to an antigen (e.g., TNF). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a single domain or dAb fragment (Ward et al., (1989) *Nature* 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins. Antibodies can be of different isotype, for example, an IgG (e.g., an IgG1, IgG2, IgG3, or IgG4 subtype), IgA1, IgA2, IgD, IgE, or IgM antibody.

The term "immunobinder" refers to a molecule that contains all or a part of the antigen binding site of an antibody, e.g. all or part of the heavy and/or light chain variable domain, such that the immunobinder specifically recognizes a target antigen. Non-limiting examples of immunobinders include full-length immunoglobulin molecules and scFvs, as well as antibody fragments, including but not limited to (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fab' fragment, which is essentially a Fab with part of the hinge region (see, FUNDAMENTAL IMMUNOLOGY (Paul ed., 3.sup.rd ed. 1993); (iv) a Fd fragment consisting of the $V_H$ and $C_H1$ domains; (v) a Fv fragment consisting of the $V_L$ and $V_H$ domains of a single arm of an antibody, (vi) a single domain antibody such as a Dab fragment (Ward et al., (1989) *Nature* 341:544-546), which consists of a $V_H$ or $V_L$ domain, a Camelid (see Hamers-Casterman, et al., Nature 363:446-448 (1993), and Dumoulin, et al., Protein Science 11:500-515 (2002)) or a Shark antibody (e.g., shark Ig-NARs Nanobodies®; and (vii) a nanobody, a heavy chain variable region containing a single variable domain and two constant domains.

The term "single chain antibody", "single chain Fv" or "scFv" refers to a molecule comprising an antibody heavy chain variable domain (or region; $V_H$) and an antibody light chain variable domain (or region; $V_L$) connected by a linker. Such scFv molecules can have the general structures: $NH_2$-$V_L$-linker-$V_H$-COOH or $NH_2$-$V_H$-linker-$V_L$-COOH. A suitable state of the art linker consists of repeated GGGGS amino acid sequences or variants thereof. In a preferred embodiment of the present invention a $(GGGGS)_4$ linker of the amino acid sequence set forth in SEQ ID NO: 8 is used, but variants of 1-3 repeats are also possible (Holliger et al. (1993), Proc. Natl. Acad. Sci. USA 90:6444-6448). Other linkers that can be used for the present invention are described by Alfthan et al. (1995), Protein Eng. 8:725-731, Choi et al. (2001), Eur. J. Immunol. 31:94-106, Hu et al. (1996), Cancer Res. 56:3055-3061, Kipriyanov et al. (1999), J. Mol. Biol. 293:41-56 and Roovers et al. (2001), Cancer Immunol.

As used herein, the term "functional property" is a property of a polypeptide (e.g., an immunobinder) for which an improvement (e.g., relative to a conventional polypeptide) is desirable and/or advantageous to one of skill in the art, e.g., in order to improve the manufacturing properties or therapeutic efficacy of the polypeptide. In one embodiment, the functional property is stability (e.g., thermal stability). In another embodiment, the functional property is solubility (e.g., under cellular conditions). In yet another embodiment, the functional property is aggregation behavior. In still another embodiment, the functional property is protein expression (e.g., in a prokaryotic cell). In yet another embodiment the functional property is refolding behavior following inclusion body solubilization in a manufacturing process. In certain embodiments, the functional property is not an improvement in antigen binding affinity. In another preferred embodiment, the improvement of one or more functional properties has no substantial effect on the binding affinity of the immunobinder.

The term "CDR" refers to one of the six hypervariable regions within the variable domains of an antibody that mainly contribute to antigen binding. One of the most commonly used definitions for the six CDRs was provided by Kabat E. A. et al., (1991) Sequences of proteins of immunological interest. NIH Publication 91-3242). As used herein, Kabat's definition of CDRs only apply for CDR1, CDR2 and CDR3 of the light chain variable domain (CDR L1, CDR L2, CDR L3, or L1, L2, L3), as well as for CDR2 and CDR3 of the heavy chain variable domain (CDR H2, CDR H3, or H2, H3). CDR1 of the heavy chain variable domain (CDR H1 or H1), however, as used herein is defined by the residue positions (Kabat numbering) starting with position 26 and ending prior to position 36. This definition is basically a fusion of CDR H1 as differently defined by Kabat and Chotia (see also FIG. 1 for illustration).

The term "antibody framework" as used herein refers to the part of the variable domain, either VL or VH, which serves as a scaffold for the antigen binding loops (CDRs) of this variable domain. In essence it is the variable domain without the CDRs.

The term "epitope" or "antigenic determinant" refers to a site on an antigen to which an immunoglobulin or antibody specifically binds (e.g., a specific site on the TNF molecule). An epitope typically includes at least 3, 4, 5, 6, 7, 8, 9, 10, 11, 12, 13, 14 or 15 consecutive or non-consecutive amino acids in a unique spatial conformation. See, e.g., *Epitope Mapping Protocols in Methods in Molecular Biology*, Vol. 66, G. E. Morris, Ed. (1996).

The terms "specific binding," "selective binding," "selectively binds," and "specifically binds," refer to antibody binding to an epitope on a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower. The term "$K_D$" or "Kd" refers to the dissociation equilibrium constant of a particular antibody-antigen interaction. Typically, the antibodies of the invention bind to TNF with a dissociation equilibrium constant ($K_D$) of less than approximately $10^{-7}$ M, such as less than approximately $10^{-8}$ M, $10^{-9}$ M or $10^{-10}$ M or even lower, for example, as determined using surface plasmon resonance (SPR) technology in a BIACORE instrument.

The term "nucleic acid molecule," as used herein refers to DNA molecules and RNA molecules. A nucleic acid molecule may be single-stranded or double-stranded, but preferably is double-stranded DNA. A nucleic acid is "operably linked" when it is placed into a functional relationship with another nucleic acid sequence. For instance, a promoter or enhancer is operably linked to a coding sequence if it affects the transcription of the sequence.

The term "vector," refers to a nucleic acid molecule capable of transporting another nucleic acid to which it has been linked. In one embodiment, the vector is a "plasmid," which refers to a circular double stranded DNA loop into which additional DNA segments may be ligated. In another embodiment, the vector is a viral vector, wherein additional DNA segments may be ligated into the viral genome. The vectors disclosed herein can be capable of autonomous replication in a host cell into which they are introduced (e.g., bacterial vectors having a bacterial origin of replication and episomal mammalian vectors) or can be can be integrated into the genome of a host cell upon introduction into the host cell, and thereby are replicated along with the host genome (e.g., non-episomal mammalian vectors).

The term "host cell" refers to a cell into which an expression vector has been introduced. Host cells include bacterial, microbial, plant or animal cells, preferably, *Escherichia coli, Bacillus subtilis; Saccharomyces cerevisiae, Pichia pastoris*, CHO (Chinese Hamster Ovary lines) or NS0 cells.

The term "lagomorphs" refers to members of the taxonomic order Lagomorpha, comprising the families Leporidae (e.g. hares and rabbits), and the Ochotonidae (pikas). In a most preferred embodiment, the lagomorphs is a rabbit. The term "rabbit" as used herein refers to an animal belonging to the family of the leporidae.

As used herein, "identity" refers to the sequence matching between two polypeptides, molecules or between two nucleic acids. When a position in both of the two compared sequences is occupied by the same base or amino acid monomer subunit (for instance, if a position in each of two polypeptides is occupied by a lysine), then the respective molecules are identical at that position. The "percentage identity" between two sequences is a function of the number of identical positions shared by the sequences, taking into account the number of gaps, and the length of each gap, which need to be introduced for optimal alignment of the two sequences. Generally, a comparison is made when two sequences are aligned to give maximum identity. Such alignment can be provided using, for instance, the method of the Needleman and Wunsch (J. Mol. Biol. (48):444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

Various aspects of the invention are described in further detail in the following subsections. It is understood that the various embodiments, preferences and ranges may be combined at will. Further, depending of the specific embodiment, selected definitions, embodiments or ranges may not apply.

If not otherwise stated, the amino acid positions are indicated according to the AHo numbering scheme. The AHo numbering system is described further in Honegger, A. and Pluckthun, A. (2001) J. Mol. Biol. 309:657-670). Alternatively, the Kabat numbering system as described further in Kabat et al. (Kabat, E. A., et al. (1991) Sequences of Proteins of Immunological Interest, Fifth Edition, U.S. Department of Health and Human Services, NIH Publication No. 91-3242) may be used. Conversion tables for the two different numbering systems used to identify amino acid residue positions in antibody heavy and light chain variable regions are provided in A. Honegger, J. Mol. Biol. 309 (2001) 657-670.

In a first aspect, the present invention provides a human acceptor framework sequence for the grafting of CDRs from lagomorph species, for example, from rabbit. The human single-chain VH framework a58 (SEQ ID NO: 1) was surprisingly found to be in essence highly compatible with the antigen-binding sites of rabbit antibodies. Therefore, the a58 VH represents a suitable scaffold to construct stable humanized scFv antibody fragments derived from grafting of rabbit loops.

Thus, in one aspect, the invention provides an immunobinder acceptor framework, comprising a VH sequence having at least 70% identity to SEQ ID No. 1.

Said sequence may be combined with any other suitable variable light chain. A preferred variable light chain is SEQ ID NO: 2 which was also disclosed in WO03/097697 and designated KI27, or any other VL sequence as disclosed in WO03/097697.

In a preferred embodiment, the variable heavy chain framework is linked to a variable light chain framework via a linker. The linker may be any suitable linker, for example a linker comprising 1 to 4 repeats of the sequence GGGGS (SEQ ID NO: 5), preferably a (GGGGS)$_4$ peptide (SEQ ID NO: 4), or a linker as disclosed in Alfthan et al. (1995) Protein Eng. 8:725-731.

Accordingly, the present invention provides an immunobinder acceptor framework comprising (i) a variable heavy chain framework having at least 70% identity, preferably at least 75%, 80%, 85%, 90%, more preferably at least 95% identity, to SEQ ID No. 1; and/or (ii) a variable light chain framework having at least 70% identity, preferably at least 75%, 80%, 85%, 90%, more preferably at least 95% identity, to SEQ ID No. 2.

In a much preferred embodiment, the invention provides an immunobinder, having a sequence with at least 60%, more preferably at least 65%, 70%, 75%, 80%, 85%, 90%, 95%, identity to SEQ ID NO: 3.

The framework is compatible with virtually any rabbit CDRs. Containing different rabbit CDRs, it is well expressed and good produced contrary to the rabbit wild type single chains and still almost fully retains the affinity of the original donor rabbit antibodies.

The immunobinder acceptor frameworks as described herein may comprise solubility enhancing substitution in the heavy chain framework, preferably at positions 12, 103 and 144 (AHo numbering). Preferably, a hydrophobic amino acid is substituted by a more hydrophilic amino acid. Hydrophilic amino acids are e.g. Arginine (R), Asparagine (N), Aspartic acid (D), Glutamine (Q), Glycine (G), Histidine (H), Lysine (K), Serine (S) and Threonine (T). More preferably, the heavy chain framework comprises (a) Serine (S) at position 12; (b) Serine (S) or Threonine (T) at position 103 and/or (c) Serine (S) or Threonine (T) at position 144.

Moreover, stability enhancing amino acids may be present at one or more positions 1, 3, 4, 10, 47, 57, 91 and 103 of the variable light chain framework (AHo numbering). More preferably, the variable light chain framework comprises glutamic acid (E) at position 1, valine (V) at position 3, leucine (L) at position 4, Serine (S) at position 10; Arginine (R) at position 47, Serine (S) at position 57, phenylalanine (F) at position 91 and/or Valine (V) at position 103.

As glutamine (Q) is prone to desamination, in another preferred embodiment, the VH comprises at position 141 a glycine (G). This substitution may improve long-term storage of the protein.

For example, the acceptor frameworks disclosed herein can be used to generate a human or humanized antibody which retains the binding properties of the non-human antibody from which the non-human CDRs are derived. Accordingly, in a preferred embodiment the invention encompasses an immunobinder acceptor framework as disclosed herein, further comprising heavy chain CDR1, CDR2 and CDR3 and/or light chain CDR1, CDR2 and CDR3 from a donor immunobinder, preferably from a mammalian immunobinder, more preferably from a lagomorph immunobinder and most preferably from a rabbit. Thus, in one embodiment, the invention provides an immunobinder specific to a desired antigen comprising (i) variable light chain CDRs of a lagomorph; and (ii) a human variable heavy chain framework having at least 70%, preferably at least 75%, 80%, 85%, 90%, 95%, and most preferably 100% identity to SEQ ID NO: 1.

Preferably, the lagomorph is a rabbit. More preferably, the immunobinder comprises heavy chain CDR1, CDR2 and CDR3 and light chain CDR1, CDR2 and CDR3 from the donor immunobinder.

As known in the art, many rabbit VH chains have extra paired cysteines relative to the murine and human counterparts. In addition to the conserved disulfide bridge formed between cys22 and cys92, there is also a cys21-cys79 bridge as well as an interCDR S-S bridge formed between the last residue of CDRH1 and the first residue of CDR H2 in some rabbit chains. Besides, pairs of cysteine residues in the CDR-L3 are often found. Besides, many rabbit antibody CDRs do not belong to any previously known canonical structure. In particular the CDR-L3 is often much longer than the CDR-L3 of a human or murine counterpart.

As stated before, the grafting of the non-human CDRs onto the frameworks disclosed herein yields a molecule wherein the CDRs are displayed in a proper conformation. If required, the affinity of the immunobinder may be improved by grafting antigen interacting framework residues of the non-human donor immunobinder. These positions may e.g. be identified by (i) identifying the respective germ line progenitor sequence or, alternatively, by using the consensus sequences in case of highly homologous framework sequences;

(ii) generating a sequence alignment of donor variable domain sequences with germ line progenitor sequence or consensus sequence of step (i); and (iii) identifying differing residues.

Differing residues on the surface of the molecule were in many cases mutated during the affinity generation process in vivo, presumably to generate affinity to the antigen.

In another aspect, the present invention provides an immunobinder which comprises the immunobinder acceptor framework described herein. Said immunobinder may e.g. be a scFv antibody, a full-length immunoglobulin, a Fab fragment, a Dab or a Nanobody.

In a preferred embodiment, the immunobinder is attached to one or more molecules, for example a therapeutic agent such as a cytotoxic agent, a cytokine, a chemokine, a growth factor or other signaling molecule, an imaging agent or a second protein such as a transcriptional activator or a DNA-binding domain.

The immunobinder as disclosed herein may e.g. be used in diagnostic applications, therapeutic application, target validation or gene therapy.

The invention further provides an isolated nucleic acid encoding the immunobinder acceptor framework disclosed herein or the immunobinder(s) as disclosed herein.

In another embodiment, a vector is provided which comprises the nucleic acid disclosed herein.

The nucleic acid or the vector as disclosed herein can e.g. be used in gene therapy.

The invention further encompasses a host cell comprising the vector and/or the nucleic acid disclosed herein.

Moreover, a composition is provided, comprising the immunobinder acceptor framework as disclosed herein, the immunobinder as disclosed herein, the isolated nucleic acid as disclosed herein or the vector as disclosed herein.

The sequences disclosed herein are the following (X residues are CDR insertion sites and contain at least 3 and up to 50 amino acids):

```
SEQ ID NO: 1: variable heavy chain framework a58
EVQLVESGGGLVQPGGSLRLSCAAS(X)_{n=3-50}

WVRQAPGKGLEWVS(X)_{n=3-50}

RFSVSRDNSKNTVYLQINSLRAEDTAVYYCAM(X)_{n=3-50}

WGQGTLVTVSS

SEQ ID NO: 2: variable light chain framework KI27
EIVMTQSPSTLSASVGDRVIITC(X)_{n=3-50}

WYQQKPGKAPKLLIY(X)_{n=3-50}

GVPSRFSGSGSGAEFTLTISSLQPDDFATYYC(X)_{n=3-50}

FGQGTKLT VLG

SEQ ID NO: 3: framework sequence
EIVMTQSPSTLSASVGDRVIITC(X)_{n=3-50}

WYQQKPGKAPKLLIY(X)_{n=3-50}

GVPSRFSGSGSGAEFTLTISSLQPDDFATYYC(X)_{n=3-50}

FGQGTKLT

VLGGGGSGGGGSGGGGSGGGGS

EVQLVESGGGLVQPGGSLRLSCAAS(X)_{n=3-50}

WVRQAPGKGLEWVS(X)_{n=3-50}

RFSVSRDNSKNTVYLQINSLRAEDTAVYYCAM(X)_{n=3-50}

WGQGTLVTVSS

SEQ ID NO: 4: linker
GGGGSGGGGSGGGGSGGGGS
```

In another aspect, the invention provides methods for the humanization of non-human antibodies by grafting CDRs of non-human donor antibodies onto stable and soluble antibody frameworks. In a particularly preferred embodiment, the CDRs stem from rabbit antibodies and the frameworks are those described above.

A general method for grafting CDRs into human acceptor frameworks has been disclosed by Winter in U.S. Pat. No. 5,225,539 and by Queen et al. in WO9007861A1, which are hereby incorporated by reference in their entirety. The general strategy for grafting CDRs from rabbit monoclonal antibodies onto selected frameworks is related to that of Winter et al. and Queen et al., but diverges in certain key respects. In particular, the methods of the invention diverge from the typical Winter and Queen methodology known in the art in that the human antibody frameworks as disclosed herein are particularly suitable as acceptors for human or non-human donor antibodies. Thus, unlike the general method of Winter and Queen, the framework sequence used for the humanization methods of the invention is not necessarily the framework sequence which exhibits the greatest sequence similarity to the sequence of the non-human (e.g., rabbit) antibody from which the donor CDRs are derived. In addition, framework residue grafting from the donor sequence to support CDR conformation is not required. At most, antigen binding amino acids located in the framework or other mutations that occurred during somatic hypermutation may be introduced.

Particular details of the grafting methods to generate humanized rabbit-derived antibodies with high solubility and stability are described below.

In exemplary embodiments of the methods of the invention, the amino acid sequence of the CDR donor antibody is first identified and the sequences aligned using conventional sequence alignment tools (e.g., Needleman-Wunsch algorithm and Blossum matrices). The introduction of gaps and nomenclature of residue positions may be done using a conventional antibody numbering system. For example, the AHo numbering system for immunoglobulin variable domains may be used. The Kabat numbering scheme may also be applied since it is the most widely adopted standard for numbering the residues in an antibody. Kabat numbering may e.g. be assigned using the SUBIM program. This program analyses variable regions of an antibody sequence and numbers the sequence according to the system established by Kabat and co-workers (Deret et al 1995). The definition of framework and CDR regions is generally done following the Kabat definition which is based on sequence variability and is the most commonly used. However, for CDR-H1, the designation is preferably a combination of the definitions of Kabat's, mean contact data generated by analysis of contacts between antibody and antigen of a subset of 3D complex structures (MacCallum et al., 1996) and Chotia's which is based on the location of the structural loop regions (see also FIG. 1). Conversion tables for the two different numbering systems used to identify amino acid residue positions in antibody heavy and light chain variable regions are provided in A. Honegger, J. Mol. Biol. 309 (2001) 657-670. The Kabat numbering system is described further in Kabat et al. (Kabat, E. A., et al. (1991) Sequences of Proteins of Immunological Interest, Fifth Edition, U.S. Department of Health and Human Services, NIH Publication No. 91-3242). The AHo numbering system is described further in Honegger, A. and Pluckthun, A. (2001) *J. Mol. Biol.* 309:657-670).

The variable domains of the rabbit monoclonal antibodies may e.g. be classified into corresponding human sub-groups using e.g. an EXCEL implementation of sequence analysis algorithms and classification methods based on analysis of the human antibody repertoire (Knappik et al., 2000, *J Mol Biol*. February 11; 296(1):57-86).

CDR conformations may be assigned to the donor antigen binding regions, subsequently residue positions required to maintain the different canonical structures can also be identified. The CDR canonical structures for five of the six antibody hypervariable regions of rabbit antibodies (L1, L2, L3, H1 and H2) are determined using Chothia's (1989) definition.

The antibodies of the invention may be further optimized to show enhanced functional properties, e.g., enhanced solubility and/or stability. In certain embodiments, the antibodies of the invention are optimized according to the "functional consensus" methodology disclosed in PCT Application Serial No. PCT/EP2008/001958, entitled "Sequence Based Engineering and Optimization of Single Chain Antibodies", filed on Mar. 12, 2008, which is incorporated herein by reference.

Exemplary framework residue positions for substitution and exemplary framework substitutions are described in PCT Application No. PCT/CH2008/000285, entitled "Methods of Modifying Antibodies, and Modified Antibodies with Improved Functional Properties", filed on Jun. 25, 2008, and PCT Application No. PCT/CH2008/000284, entitled "Sequence Based Engineering and Optimization of Single Chain Antibodies", filed on Jun. 25, 2008.

In other embodiments, the immunobinders of the invention comprise one or more of the stability enhancing mutations described in U.S. Provisional Application Ser. No. 61/075,692, entitled "Solubility Optimization of Immunobinders", filed on Jun. 25, 2008. In certain preferred embodiments, the immunobinder comprises a solubility enhancing mutation at an amino acid position selected from the group of heavy chain amino acid positions consisting of 12, 103 and 144 (AHo Numbering convention). In one preferred embodiment, the immunobinder comprises one or more substitutions selected from the group consisting of: (a) Serine (S) at heavy chain amino acid position 12; (b) Serine (S) or Threonine (T) at heavy chain amino acid position 103; and (c) Serine (S) or Threonine (T) at heavy chain amino acid position 144. In another embodiment, the immunobinder comprises the following substitutions: (a) Serine (S) at heavy chain amino acid position 12; (b) Serine (S) or Threonine (T) at heavy chain amino acid position 103; and (c) Serine (S) or Threonine (T) at heavy chain amino acid position 144.

In certain preferred embodiments, the immunobinder comprises stability enhancing mutations at a framework residue of the light chain acceptor framework in at least one of positions 1, 3, 4, 10, 47, 57, 91 and 103 of the light chain variable region according to the AHo numbering system. In a preferred embodiment, the light chain acceptor framework comprises one or more substitutions selected from the group consisting of (a) glutamic acid (E) at position 1, (b) valine (V) at position 3, (c) leucine (L) at position 4; (d) Serine (S) at position 10; (e) Arginine (R) at position 47; (e) Serine (S) at position 57; (f) phenylalanine (F) at position 91; and (g) Valine (V) at position 103.

One can use any of a variety of available methods to produce a humanized antibody comprising a mutation as described above.

Accordingly, the present invention provides an immunobinder humanized according to the method described herein.

In certain preferred embodiments, the target antigen of said immunobinder is VEGF or TNFα.

The polypeptides described in the present invention or generated by a method of the present invention can, for example, be synthesized using techniques known in the art. Alternatively nucleic acid molecules encoding the desired variable regions can be synthesized and the polypeptides produced by recombinant methods.

For example, once the sequence of a humanized variable region has been decided upon, that variable region or a polypeptide comprising it can be made by techniques well known in the art of molecular biology. More specifically, recombinant DNA techniques can be used to produce a wide range of polypeptides by transforming a host cell with a nucleic acid sequence (e.g., a DNA sequence that encodes the desired variable region (e.g., a modified heavy or light chain; the variable domains thereof, or other antigen-binding fragments thereof)).

In one embodiment, one can prepare an expression vector including a promoter that is operably linked to a DNA sequence that encodes at least $V_H$ or $V_L$. If necessary, or desired, one can prepare a second expression vector including a promoter that is operably linked to a DNA sequence that encodes the complementary variable domain (i.e., where the parent expression vector encodes $V_H$, the second expression vector encodes $V_L$ and vice versa). A cell line (e.g., an immortalized mammalian cell line) can then be transformed with one or both of the expression vectors and cultured under conditions that permit expression of the chimeric variable domain or chimeric antibody (see, e.g., International Patent Application No. PCT/GB85/00392 to Neuberger et. al.).

In one embodiment, variable regions comprising donor CDRs and acceptor FR amino acid sequences can be made and then changes introduced into the nucleic acid molecules to effect the CDR amino acid substitution.

Exemplary art recognized methods for making a nucleic acid molecule encoding an amino acid sequence variant of a polypeptide include, but are not limited to, preparation by site-directed (or oligonucleotide-mediated) mutagenesis, PCR mutagenesis, and cassette mutagenesis of an earlier prepared DNA encoding the polypeptide.

Site-directed mutagenesis is a preferred method for preparing substitution variants. This technique is well known in the art (see, e.g., Carter et al. Nucleic Acids Res. 13:4431-4443 (1985) and Kunkel et al., Proc. Natl. Acad. Sci. USA 82:488 (1987)). Briefly, in carrying out site-directed mutagenesis of DNA, the parent DNA is altered by first hybridizing an oligonucleotide encoding the desired mutation to a single strand of such parent DNA. After hybridization, a DNA polymerase is used to synthesize an entire second strand, using the hybridized oligonucleotide as a primer, and using the single strand of the parent DNA as a template. Thus, the oligonucleotide encoding the desired mutation is incorporated in the resulting double-stranded DNA.

PCR mutagenesis is also suitable for making amino acid sequence variants of polypeptides. See Higuchi, in PCR Protocols, pp. 177-183 (Academic Press, 1990); and Vallette et al., Nuc. Acids Res. 17:723-733 (1989). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al., Gene 34:315-323 (1985). The starting material is the plasmid (or other vector) comprising the DNA to be mutated. The codon(s) in the parent DNA to be mutated are identified.

There must be a unique restriction endonuclease site on each side of the identified mutation site(s). If no such restriction sites exist, they may be generated using the above-described oligonucleotide-mediated mutagenesis method to introduce them at appropriate locations in the DNA encoding the polypeptide. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

A variable region generated by the methods of the invention can be re-modeled and further altered to further increase antigen binding. Thus, the steps described above can be preceded or followed by additional steps, including, e.g. affinity maturation. In addition, empirical binding data can be used for further optimization.

Aside from amino acid substitutions, the present invention contemplates other modifications, e.g., to Fc region amino acid sequences in order to generate an Fc region variant with altered effector function. One may, for example, delete one or more amino acid residues of the Fc region in order to reduce or enhance binding to an FcR. In one embodiment, one or more of the Fc region residues can be modified in order to generate such an Fc region variant. Generally, no more than one to about ten Fc region residues will be deleted according to this embodiment of the invention. The Fc region herein comprising one or more amino acid deletions will preferably retain at least about 80%, and preferably at least about 90%, and most preferably at least about 95%, of the starting Fc region or of a native sequence human Fc region.

In one embodiment, the polypeptides described in the present invention or generated by a method of the present invention, e.g., humanized Ig variable regions and/or polypeptides comprising humanized Ig variable regions may be produced by recombinant methods. For example, a polynucleotide sequence encoding a polypeptide can be inserted in a suitable expression vector for recombinant expression. Where the polypeptide is an antibody, polynucleotides encoding additional light and heavy chain variable regions, optionally linked to constant regions, may be inserted into the same or different expression vector. An affinity tag sequence (e.g. a His(6) tag) may optionally be attached or included within the polypeptide sequence to facilitate downstream purification. The DNA segments encoding immunoglobulin chains are the operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the polypeptide.

These expression vectors are typically replicable in the host organisms either as episomes or as an integral part of the host chromosomal DNA. Commonly, expression vectors contain selection markers (e.g., ampicillin-resistance, hygromycin-resistance, tetracycline resistance or neomycin resistance) to permit detection of those cells transformed with the desired DNA sequences (see, e.g., U.S. Pat. No. 4,704,362).

*E. coli* is one prokaryotic host particularly useful for cloning the polynucleotides (e.g., DNA sequences) of the present invention. Other microbial hosts suitable for use include bacilli, such as *Bacillus subtilus*, and other enterobacteriaceae, such as *Salmonella, Serratia*, and various *Pseudomonas* species.

Other microbes, such as yeast, are also useful for expression. *Saccharomyces* and *Pichia* are exemplary yeast hosts, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for methanol, maltose, and galactose utilization.

Within the scope of the present invention, *E. coli* and *S. cerevisiae* are preferred host cells.

In addition to microorganisms, mammalian tissue culture may also be used to express and produce the polypeptides of the present invention (e.g., polynucleotides encoding immunoglobulins or fragments thereof). See Winnacker, From Genes to Clones, VCH Publishers, N.Y., N.Y. (1987). Eukaryotic cells are actually preferred, because a number of suitable host cell lines capable of secreting heterologous proteins (e.g., intact immunoglobulins) have been developed in the art, and include CHO cell lines, various Cos cell lines, HeLa cells, 293 cells, myeloma cell lines, transformed B-cells, and hybridomas. Expression vectors for these cells can include expression control sequences, such as an origin of replication, a promoter, and an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. See Co et al., *J. Immunol.* 148:1149 (1992).

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., *Molecular Cloning: A Laboratory Manual* (Cold Spring Harbor Press, 2nd ed., 1989). Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

The subject polypeptide can also be incorporated in transgenes for introduction into the genome of a transgenic animal and subsequent expression, e.g., in the milk of a transgenic animal (see, e.g., Deboer et al. U.S. Pat. No. 5,741,957; Rosen U.S. Pat. No. 5,304,489; and Meade U.S. Pat. No. 5,849,992. Suitable transgenes include coding sequences for light and/or heavy chains in operable linkage with a promoter and enhancer from a mammary gland specific gene, such as casein or beta lactoglobulin.

Polypeptides can be expressed using a single vector or two vectors. For example, antibody heavy and light chains may be cloned on separate expression vectors and co-transfected into cells.

In one embodiment, signal sequences may be used to facilitate expression of polypeptides of the invention.

Once expressed, the polypeptides can be purified according to standard procedures of the art, including ammonium sulfate precipitation, affinity columns (e.g., protein A or protein G), column chromatography, HPLC purification, gel electrophoresis and the like (see generally Scopes, Protein Purification (Springer-Verlag, N.Y., (1982)).

Either the humanized Ig variable regions or polypeptides comprising them can be expressed by host cells or cell lines in culture. They can also be expressed in cells in vivo. The cell line that is transformed (e.g., transfected) to produce the altered antibody can be an immortalized mammalian cell line, such as those of lymphoid origin (e.g., a myeloma, hybridoma, trioma or quadroma cell line). The cell line can also include normal lymphoid cells, such as B-cells, that have been immortalized by transformation with a virus (e.g., the Epstein-Barr virus).

Although typically the cell line used to produce the polypeptide is a mammalian cell line, cell lines from other sources (such as bacteria and yeast) can also be used. In particular, *E. coli*-derived bacterial strains can be used, especially, e.g., phage display.

Some immortalized lymphoid cell lines, such as myeloma cell lines, in their normal state, secrete isolated Ig light or heavy chains. If such a cell line is transformed with a vector that expresses an altered antibody, prepared during the process of the invention, it will not be necessary to carry out the remaining steps of the process, provided that the normally secreted chain is complementary to the variable domain of the Ig chain encoded by the vector prepared earlier.

If the immortalized cell line does not secrete or does not secrete a complementary chain, it will be necessary to introduce into the cells a vector that encodes the appropriate complementary chain or fragment thereof.

In the case where the immortalized cell line secretes a complementary light or heavy chain, the transformed cell line may be produced for example by transforming a suitable bacterial cell with the vector and then fusing the bacterial cell with the immortalized cell line (e.g., by spheroplast fusion). Alternatively, the DNA may be directly introduced into the immortalized cell line by electroporation.

In one embodiment, a humanized Ig variable region as described in the present invention or generated by a method of the present invention can be present in an antigen-binding fragment of any antibody. The fragments can be recombinantly produced and engineered, synthesized, or produced by digesting an antibody with a proteolytic enzyme. For example, the fragment can be a Fab fragment; digestion with papain breaks the antibody at the region, before the interchain (i.e., $V_H$-$V_H$) disulphide bond, that joins the two heavy chains. This results in the formation of two identical fragments that contain the light chain and the $V_H$ and $C_H1$ domains of the heavy chain. Alternatively, the fragment can be an F(ab')$_2$ fragment. These fragments can be created by digesting an antibody with pepsin, which cleaves the heavy chain after the inter-chain disulfide bond, and results in a fragment that contains both antigen-binding sites. Yet another alternative is to use a "single chain" antibody. Single-chain Fv (scFv) fragments can be constructed in a variety of ways. For example, the C-terminus of $V_H$ can be linked to the N-terminus of $V_L$. Typically, a linker (e.g., (GGGGS)$_4$; SEQ ID NO: 4) is placed between $V_H$ and $V_L$. However, the order in which the chains can be linked can be reversed, and tags that facilitate detection or purification (e.g., Myc-, His-, or FLAG-tags) can be included (tags such as these can be appended to any antibody or antibody fragment of the invention; their use is not restricted to scFv). Accordingly, and as noted below, tagged antibodies are within the scope of the present invention. In alternative embodiments, the antibodies described herein, or generated by the methods described herein, can be heavy chain dimers or light chain dimers. Still further, an antibody light or heavy chain, or portions thereof, for example, a single domain antibody (DAb), can be used.

In another embodiment, a humanized Ig variable region as described in the present invention or generated by a method of the present invention is present in a single chain antibody (ScFv) or a minibody (see e.g., U.S. Pat. No. 5,837,821 or WO 94/09817A1). Minibodies are dimeric molecules made up of two polypeptide chains each comprising an ScFv molecule (a single polypeptide comprising one or more antigen binding sites, e.g., a $V_L$ domain linked by a flexible linker to a $V_H$ domain fused to a CH3 domain via a connecting peptide). ScFv molecules can be constructed in a $V_H$-linker-$V_L$ orientation or $V_L$-linker-$V_H$ orientation. The flexible hinge that links the $V_L$ and $V_H$ domains that make up the antigen binding site preferably comprises from about 10 to about 50 amino acid residues. An exemplary connecting peptide for this purpose is (Gly4Ser)3 (Huston et al. (1988). *PNAS*, 85:5879). Other connecting peptides are known in the art.

Methods of making single chain antibodies are well known in the art, e.g., Ho et al. (1989), *Gene*, 77:51; Bird et al. (1988), *Science* 242:423; Pantoliano et al. (1991), *Biochemistry* 30:10117; Milenic et al. (1991), *Cancer Research*, 51:6363; Takkinen et al. (1991), *Protein Engineering* 4:837. Minibodies can be made by constructing an ScFv component and connecting peptide-CH$_3$ component using methods described in the art (see, e.g., U.S. Pat. No. 5,837,821 or WO 94/09817A1). These components can be isolated from separate plasmids as restriction fragments and then ligated and recloned into an appropriate vector. Appropriate assembly can be verified by restriction digestion and DNA sequence analysis. In one embodiment, a minibody of the invention comprises a connecting peptide. In one embodiment, the connecting peptide comprises a Gly/Ser linker, e.g., GGGSSGGGSGG (SEQ ID NO: 6).

In another embodiment, a tetravalent minibody can be constructed. Tetravalent minibodies can be constructed in the same manner as minibodies, except that two ScFv molecules are linked using a flexible linker, e.g., having an amino acid sequence (G$_4$S)$_4$G$_3$AS (SEQ ID NO: 7).

In another embodiment, a humanized variable region as described in the present invention or generated by a method of the present invention can be present in a diabody. Diabodies are similar to scFv molecules, but usually have a short (less than 10 and preferably 1-5) amino acid residue linker connecting both variable domains, such that the $V_L$ and $V_H$ domains on the same polypeptide chain can not interact. Instead, the $V_L$ and $V_H$ domain of one polypeptide chain interact with the $V_H$ and $V_L$ domain (respectively) on a second polypeptide chain (WO 02/02781).

In another embodiment, a humanized variable region of the invention can be present in an immunoreactive fragment or portion of an antibody (e.g. an scFv molecule, a minibody, a tetravalent minibody, or a diabody) operably linked to an FcR binding portion. In an exemplary embodiment, the FcR binding portion is a complete Fc region.

Preferably, the humanization methods described herein result in Ig variable regions in which the affinity for antigen is not substantially changed compared to the donor antibody.

In one embodiment, polypeptides comprising the variable domains of the instant invention bind to antigens with a binding affinity greater than (or equal to) an association constant Ka of about $10^5$ M$^{-1}$, $10^6$ M$^{-1}$, $10^7$ M$^{-1}$, $10^8$ M$^{-1}$, $10^9$ M$^{-1}$, $10^{10}$ M$^{-1}$, $10^{11}$ M$^{-1}$, or $10^{12}$ M$^{-1}$, (including affinities intermediate of these values).

Affinity, avidity, and/or specificity can be measured in a variety of ways. Generally, and regardless of the precise manner in which affinity is defined or measured, the methods of the invention improve antibody affinity when they generate an antibody that is superior in any aspect of its clinical application to the antibody (or antibodies) from which it was made (for example, the methods of the invention are considered effective or successful when a modified antibody can be administered at a lower dose or less frequently or by a more convenient route of administration than an antibody (or antibodies) from which it was made).

More specifically, the affinity between an antibody and an antigen to which it binds can be measured by various assays, including, e.g., an ELISA assay, a BiaCore assay or the KinExA™ 3000 assay (available from Sapidyne Instruments (Boise, Id.)). Briefly, sepharose beads are coated with antigen (the antigen used in the methods of the invention can be any antigen of interest (e.g., a cancer antigen; a cell surface protein or secreted protein; an antigen of a pathogen (e.g., a bacterial or viral antigen (e.g., an HIV antigen, an influenza antigen, or a hepatitis antigen)), or an allergen) by covalent attachment. Dilutions of antibody to be tested are prepared and each dilution is added to the designated wells on a plate. A detection antibody (e.g. goat anti-human IgG-HRP conjugate) is then added to each well followed by a chromagenic substrate (, e.g. HRP). The plate is then read in ELISA plate reader at 450 nM, and EC50 values are calculated. (It is understood, however, that the methods described here are generally applicable; they are not limited to the production of antibodies that bind any particular antigen or class of antigens.)

Those of ordinary skill in the art will recognize that determining affinity is not always as simple as looking at a single FIGURE. Since antibodies have two arms, their apparent affinity is usually much higher than the intrinsic affinity between the variable region and the antigen (this is believed to be due to avidity). Intrinsic affinity can be measured using scFv or Fab fragments.

In another aspect, the present invention features a humanized rabbit antibody, or a fragment thereof, conjugated to a therapeutic moiety, such as a cytotoxin, a drug (e.g., an immunosuppressant) or a radiotoxin. Such conjugates are referred to herein as "immunoconjugates".

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in *Monoclonal Antibodies And Cancer Therapy*, Reisfeld et al. (eds.), pp. 243-56 (Alan R. Liss, Inc. 1985); Hellstrom et al., "Antibodies For Drug Delivery", in *Controlled Drug Delivery* (2nd Ed.), Robinson et al. (eds.), pp. 623-53 (Marcel Dekker, Inc. 1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), pp. 303-16 (Academic Press 1985), and Thorpe et al., "The Preparation And Cytotoxic Properties Of Antibody-Toxin Conjugates", *Immunol. Rev.*, 62:119-58 (1982).

In one aspect the invention provides pharmaceutical formulations comprising humanized rabbit antibodies for the treatment disease. The term "pharmaceutical formulation" refers to preparations which are in such form as to permit the biological activity of the antibody or antibody derivative to be unequivocally effective, and which contain no additional components which are toxic to the subjects to which the formulation would be administered. "Pharmaceutically acceptable" excipients (vehicles, additives) are those which can reasonably be administered to a subject mammal to provide an effective dose of the active ingredient employed.

EQUIVALENTS

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the invention, and exclusive use of all modifications that come within the scope of the appended claims is reserved. It is intended that the present invention be limited only to the extent required by the appended claims and the applicable rules of law.

All literature and similar material cited in this application, including, patents, patent applications, articles, books, treatises, dissertations, web pages, figures and/or appendices, regardless of the format of such literature and similar materials, are expressly incorporated by reference in their entirety. In the event that one or more of the incorporated literature and similar materials differs from or contradicts this application, including defined terms, term usage, described techniques, or the like, this application controls.

The invention claimed is:

1. An immunobinder specific to a desired antigen comprising:
   (a) a light chain acceptor framework comprising the three variable light chain CDRs of a lagomorph immunobinder specific for said desired antigen; and
   (b) a human heavy chain acceptor framework comprising SEQ ID NO: 1 and the three variable heavy chain CDRs of said lagomorph immunobinder.

2. The immunobinder of claim 1, wherein the light chain acceptor framework has at least 85% identity to SEQ ID NO: 2.

3. The immunobinder of claim 1, further comprising a linker sequence that links the variable light chain acceptor framework and the heavy chain acceptor framework, wherein the linker sequence is SEQ ID NO: 4.

4. The immunobinder of claim 1, further comprising light chain donor framework residues involved in antigen binding.

5. The immunobinder of claim 1, wherein the immunobinder is a scFv antibody, a full-length immunoglobulin or a Fab fragment.

6. A humanized immunobinder specific for a desired antigen comprising:
   (a) the three heavy chain CDRs of a donor rabbit immunobinder specific for said desired antigen grafted into a human heavy chain acceptor framework comprising SEQ ID NO: 1; and
   (b) the three light chain CDRs of said donor rabbit immunobinder grafted into a light chain acceptor framework having at least 85% identity to SEQ ID NO: 2.

* * * * *

SEQUENCE LISTING

<160> NUMBER OF SEQ ID NOS: 7

<210> SEQ ID NO 1
<211> LENGTH: 232

```
<212> TYPE: PRT
<213> ORGANISM: Artificial
<220> FEATURE:
<223> OTHER INFORMATION: variable heavy chain framework a58
<220> FEATURE:
<221> NAME/KEY: MISC_FEATURE
<222> LOCATION: (26)..(75)
<223> OTHER INFORMATION: CDR1; at least 3 and up to 50 amino acids can
      be present or absent; Xaa can be any naturally occurring amino
      acid
<220> FEATURE:
<221> NAME/KEY: MISC_FEATURE
<222> LOCATION: (90)..(139)
<223> OTHER INFORMATION: CDR2; at least 3 and up to 50 amino acids can
      be present or absent; Xaa can be any naturally occurring amino
      acid
<220> FEATURE:
<221> NAME/KEY: MISC_FEATURE
<222> LOCATION: (172)..(221)
<223> OTHER INFORMATION: CDR3; at least 3 and up to 50 amino acids can
      be present or absent; Xaa can be any naturally occurring amino
      acid

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Trp Val Arg Gln Ala
65                  70                  75                  80

Pro Gly Lys Gly Leu Glu Trp Val Ser Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Arg Phe Ser Val Ser
    130                 135                 140

Arg Asp Asn Ser Lys Asn Thr Val Tyr Leu Gln Ile Asn Ser Leu Arg
145                 150                 155                 160

Ala Glu Asp Thr Ala Val Tyr Tyr Cys Ala Met Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Trp Gly Gln
    210                 215                 220

Gly Thr Leu Val Thr Val Ser Ser
225                 230

<210> SEQ ID NO 2
<211> LENGTH: 231
<212> TYPE: PRT
<213> ORGANISM: Artificial
<220> FEATURE:
<223> OTHER INFORMATION: variable light chain framework KI27
<220> FEATURE:
<221> NAME/KEY: MISC_FEATURE
<222> LOCATION: (24)..(73)
```

<223> OTHER INFORMATION: CDR1; at least 3 and up to 50 amino acids can be present or absent; Xaa can be any naturally occurring amino acid
<220> FEATURE:
<221> NAME/KEY: MISC_FEATURE
<222> LOCATION: (89)..(138)
<223> OTHER INFORMATION: CDR2; at least 3 and up to 50 amino acids can be present or absent; Xaa can be any naturally occurring amino acid
<220> FEATURE:
<221> NAME/KEY: MISC_FEATURE
<222> LOCATION: (171)..(220)
<223> OTHER INFORMATION: CDR3; at least 3 and up to 50 amino acids can be present or absent; Xaa can be any naturally occurring amino acid

<400> SEQUENCE: 2

```
Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Trp Tyr Gln Gln Lys Pro Gly
65                  70                  75                  80

Lys Ala Pro Lys Leu Leu Ile Tyr Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Gly Val Pro Ser Arg Phe
    130                 135                 140

Ser Gly Ser Gly Ser Gly Ala Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Phe Gly Gln Gly
    210                 215                 220

Thr Lys Leu Thr Val Leu Gly
225                 230
```

<210> SEQ ID NO 3
<211> LENGTH: 483
<212> TYPE: PRT
<213> ORGANISM: Artificial
<220> FEATURE:
<223> OTHER INFORMATION: framework sequence
<220> FEATURE:
<221> NAME/KEY: MISC_FEATURE
<222> LOCATION: (24)..(73)
<223> OTHER INFORMATION: CDR1; at least 3 and up to 50 amino acids can be present or absent; Xaa can be any naturally occurring amino acid
<220> FEATURE:
<221> NAME/KEY: MISC_FEATURE
<222> LOCATION: (89)..(138)
<223> OTHER INFORMATION: CDR2; at least 3 and up to 50 amino acids can be present or absent; Xaa can be any naturally occurring amino
acid
<220> FEATURE:
<221> NAME/KEY: MISC_FEATURE
<222> LOCATION: (171)..(220)
<223> OTHER INFORMATION: CDR3; at least 3 and up to 50 amino acids can
be present or absent; Xaa can be any naturally occurring amino
acid
<220> FEATURE:
<221> NAME/KEY: MISC_FEATURE
<222> LOCATION: (277)..(326)
<223> OTHER INFORMATION: Heavy Chain CDR1; at least 3 and up to 50 amino
acids can be present or absent; Xaa can be any naturally occurring
amino acid
<220> FEATURE:
<221> NAME/KEY: MISC_FEATURE
<222> LOCATION: (341)..(390)
<223> OTHER INFORMATION: Heavy Chain CDR2; at least 3 and up to 50 amino
acids can be present or absent; Xaa can be any naturally occurring
amino acid
<220> FEATURE:
<221> NAME/KEY: MISC_FEATURE
<222> LOCATION: (423)..(472)
<223> OTHER INFORMATION: Heavy Chain CDR3; at least 3 and up to 50 amino
acids can be present or absent; Xaa can be any naturally occurring
amino acid

<400> SEQUENCE: 3

Glu Ile Val Met Thr Gln Ser Pro Ser Thr Leu Ser Ala Ser Val Gly
1               5                   10                  15

Asp Arg Val Ile Ile Thr Cys Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Trp Tyr Gln Gln Lys Pro Gly
65                  70                  75                  80

Lys Ala Pro Lys Leu Leu Ile Tyr Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Gly Val Pro Ser Arg Phe
    130                 135                 140

Ser Gly Ser Gly Ser Gly Ala Glu Phe Thr Leu Thr Ile Ser Ser Leu
145                 150                 155                 160

Gln Pro Asp Asp Phe Ala Thr Tyr Tyr Cys Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Phe Gly Gln Gly
    210                 215                 220

Thr Lys Leu Thr Val Leu Gly Gly Gly Gly Ser Gly Gly Gly Gly
225                 230                 235                 240

Ser Gly Gly Gly Gly Ser Gly Gly Gly Ser Glu Val Gln Leu Val
                245                 250                 255

Glu Ser Gly Gly Gly Leu Val Gln Pro Gly Gly Ser Leu Arg Leu Ser
                260                 265                 270

```
Cys Ala Ala Ser Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa Xaa
290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Trp Val Arg Gln Ala Pro Gly Lys Gly Leu
                325                 330                 335

Glu Trp Val Ser Xaa Xaa Xaa Xaa Xaa Xaa Xaa Xaa Xaa Xaa Xaa Xaa
                340                 345                 350

Xaa Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa Xaa
        370                 375                 380

Xaa Xaa Xaa Xaa Xaa Xaa Arg Phe Ser Val Ser Arg Asp Asn Ser Lys
385                 390                 395                 400

Asn Thr Val Tyr Leu Gln Ile Asn Ser Leu Arg Ala Glu Asp Thr Ala
                405                 410                 415

Val Tyr Tyr Cys Ala Met Xaa Xaa Xaa Xaa Xaa Xaa Xaa Xaa Xaa Xaa
            420                 425                 430

Xaa Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa Xaa
        450                 455                 460

Xaa Xaa Xaa Xaa Xaa Xaa Xaa Trp Gly Gln Gly Thr Leu Val Thr
465                 470                 475                 480

Val Ser Ser

<210> SEQ ID NO 4
<211> LENGTH: 20
<212> TYPE: PRT
<213> ORGANISM: Artificial
<220> FEATURE:
<223> OTHER INFORMATION: linker sequence

<400> SEQUENCE: 4

Gly Gly Gly Gly Ser Gly Gly Gly Ser Gly Gly Gly Ser Gly
1               5                   10                  15

Gly Gly Gly Ser
            20

<210> SEQ ID NO 5
<211> LENGTH: 5
<212> TYPE: PRT
<213> ORGANISM: Artificial
<220> FEATURE:
<223> OTHER INFORMATION: linker

<400> SEQUENCE: 5

Gly Gly Gly Gly Ser
1               5

<210> SEQ ID NO 6
<211> LENGTH: 11
<212> TYPE: PRT
<213> ORGANISM: Artificial
<220> FEATURE:
<223> OTHER INFORMATION: linker sequence

<400> SEQUENCE: 6
```

```
Gly Gly Gly Ser Ser Gly Gly Ser Gly Gly
1               5               10

<210> SEQ ID NO 7
<211> LENGTH: 25
<212> TYPE: PRT
<213> ORGANISM: Artificial
<220> FEATURE:
<223> OTHER INFORMATION: linker sequence

<400> SEQUENCE: 7

Gly Gly Gly Gly Ser Gly Gly Gly Ser Gly Gly Gly Ser Gly
1               5               10              15
Gly Gly Gly Ser Gly Gly Gly Ala Ser
            20              25
```